(12) United States Patent
Dawkins et al.

(10) Patent No.: US 11,986,031 B2
(45) Date of Patent: May 21, 2024

(54) SANITIZING FACE MASKS

(71) Applicants: Kayan Dawkins, New Rochelle, NY (US); Marsha Dawkins, New Rochelle, NY (US)

(72) Inventors: Kayan Dawkins, New Rochelle, NY (US); Marsha Dawkins, New Rochelle, NY (US)

( * ) Notice: Subject to any disclaimer, the term of this patent is extended or adjusted under 35 U.S.C. 154(b) by 751 days.

(21) Appl. No.: 17/156,993

(22) Filed: Jan. 25, 2021

(65) Prior Publication Data

US 2022/0118125 A1 Apr. 21, 2022

Related U.S. Application Data

(60) Provisional application No. 63/091,972, filed on Oct. 15, 2020.

(51) Int. Cl.
*A41D 13/11* (2006.01)
*A61L 2/00* (2006.01)

(52) U.S. Cl.
CPC .......... *A41D 13/11* (2013.01); *A41D 13/1192* (2013.01); *A61L 2/0047* (2013.01); *A61L 2202/11* (2013.01); *A61L 2202/16* (2013.01); *A61L 2202/26* (2013.01)

(58) Field of Classification Search
CPC ....... A62B 23/00; A62B 23/02; A62B 23/025; A62B 23/06; A62B 18/00; A62B 18/02; A62B 18/025; A62B 9/00; A62B 7/00; A62B 7/10; A41D 13/11; A41D 13/1107; A41D 13/1115; A41D 13/1123; A41D 13/113; A41D 13/1138; A41D 13/1146; A41D 13/1153; A41D 13/1161; A41D 13/1169; A41D 13/1176; A41D 13/1184; A41D 13/1192
See application file for complete search history.

(56) References Cited

U.S. PATENT DOCUMENTS

| | | | | |
|---|---|---|---|---|
| 5,165,395 A | * | 11/1992 | Ricci | A41D 13/1146 55/DIG. 35 |
| 2007/0000003 A1 | * | 1/2007 | DeCastro | A41D 13/1184 2/9 |
| 2007/0101867 A1 | * | 5/2007 | Hunter | A62B 23/02 96/224 |
| 2021/0275714 A1 | * | 9/2021 | Almeida | A62B 18/025 |

(Continued)

FOREIGN PATENT DOCUMENTS

CN 104826250 A * 8/2015

*Primary Examiner* — Colin W Stuart
(74) *Attorney, Agent, or Firm* — Brennan, Manna & Diamond, LLC (57) ABSTRACT

A sanitizing face mask and sanitizing device for use with a face mask. The sanitizing face mask incorporates a sanitizing component and a face mask. The sanitizing component comprises an ultraviolet (UV) generating element configured to emit a sanitizing light. The sanitizing light generates UV light capable of sanitizing air inhaled or exhaled through the face mask. The sanitizing component may be positioned within a pocket in the face mask or attached to the face mask externally. A sanitizing component protective component may encapsulate the sanitizing component to protect a user from radiation from the UV light. The pocket may also comprise a protective liner to protect the user from the radiation.

20 Claims, 5 Drawing Sheets

(56) References Cited

U.S. PATENT DOCUMENTS

2021/0275836 A1* 9/2021 Bindhammer ....... A62B 18/025
2022/0007756 A1* 1/2022 Chan .................. A41D 13/1107
2022/0016297 A1* 1/2022 Huang ..................... A61L 2/10

* cited by examiner

SANITIZING FACE MASKS

CROSS-REFERENCE TO RELATED APPLICATION

The present application claims priority to, and the benefit of, U.S. Provisional Application No. 63/091,972, which was filed on Oct. 15, 2020 and is incorporated herein by reference in its entirety.

FIELD OF THE INVENTION

The present invention generally relates to a sanitizing system for a face mask, and more specifically to a face mask with sanitization protection incorporated into the mask. Accordingly, the present specification makes specific reference thereto. However, it is to be appreciated that aspects of the present invention are also equally amenable to other like applications, devices and methods of manufacture.

BACKGROUND

By way of background, personal protective equipment (PPE) such as face masks are important in reducing the harmful spread of airborne pathogens. Standard fabric face masks may be unable to fully protect the wearer from spreading germs, viruses, and bacteria. Inhaled and exhaled air may still be dangerous to the wearer and others putting them at risk for serious illnesses. People that do not use face masks are increasingly susceptible to inhaling these harmful airborne pathogens. Protective face masks typically cover the mouth and nose protecting the respiratory tract. Not wearing a mask at all in public puts the user at risk of not complying with public health laws or recommendations in addition to the health hazards.

Germs, viruses, bacteria, microbes, and other pathogens are microscopic living things persisting everywhere in nature and are frequently airborne. A pathogen is a microorganism that has the potential to cause disease. Introducing these pathogens and organisms into the body by inhalation or through the mucus membranes can lead to serious illness or even death. Poor personal hygiene or the lack of proper personal protective equipment puts people at greater risk of infection as they breathe in these organisms especially in indoor environments or when people are in close proximity to each other.

Viruses are a common cause of infectious diseases that have a considerable impact on an individual's health. Transmission of a virus typically occurs directly from person to person, often by inhalation. COVID-19 is a virus caused by a coronavirus called SARS-CoV-2. It spreads mainly through respiratory droplets produced when an infected person coughs or sneezes. These droplets can land in the unprotected mouths or noses of people who are nearby or possibly be inhaled into the lungs. Spread of the virus is more likely when people are in close contact with one another without any protective barrier in place. Face masks are the primary physical barrier typically used to decrease or prevent this type of airborne virus transmission. Additionally, many countries and governments either recommend or even require by law the use of some kind of face mask barrier in public spaces during public health emergencies such as a pandemic or other healthcare crisis.

Disinfectants and sanitizing agents are used to clean contaminated personal protective equipment as one of the more frequently implemented measures to control transmission of pathogens in indoor environments. Disinfectants and sanitizers have proven effective at reducing the overall number of the disease causing microorganisms that cause illness on a surface or PPE. Regular and routine cleaning is necessary to prohibit the continued spread of these microorganisms. While cleaning is simple to perform, its efficacy is questionable, and in many cases is subject to time between applications, chemical performance and human error. Additionally, the cleaning effect is short lived, being limited to the point when recontamination of the surface occurs. Once a surface is contaminated again, the pathogens will continue to survive until the area is disinfected again.

Face masks are a type of PPE that have been used in the health care industry and even in public places to limit or prevent the transmission of disease for years. Health experts consistently agree that face masks prevent or at least limit the spread of disease. Face masks are beneficial as they can protect the wearer from exposure to air born transmission of disease, contaminates, and pollutants. Face masks used by an infected individual protect others as the masks contain much of the exhaled and expelled airborne respiratory droplets from the infected person.

One problem with traditional face masks is that they are typically designed for a single use or they must be cleaned between uses. This requires either using new masks or using traditional cleaning or sterilization processes which takes the mask out of use. UV light is a form of electromagnetic radiation with a wavelength shorter than that of visible light. UV light is categorized as consisting of 3 wavelength bands, each having different properties. Ninety-nine percent of the UV light that reaches the earth's surface is UV-A (400-320 nm). UV-B (320-290 nm) is responsible for skin tanning and sunburn and with long exposure may damage skin. UV-C (290-100 nm) has the highest energy of the UV light bands. The primary germicidal range for UV light is approximately 260 to 254 nm, which is within the UV-C band. The theory behind use of UV light to disinfect air is that respiratory infections may be spread by suspended aerosols.

In this manner, the improved sanitizing face mask of the present invention accomplishes all of the forgoing objectives, thereby providing an easy solution to protect a wearer and others from dangerous pathogens. A primary feature of the present invention a face mask that incorporates a sanitizing system. Finally, the improved sanitizing face mask of the present invention is capable of sanitizing inhaled and exhaled air during use.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one embodiment thereof, comprises a sanitizing face mask comprises a mask component and a sanitizing component. The sanitizing component comprises a base and an ultraviolet (UV) generating component incorporated into the base. The UV generating component comprises a plurality of light emitting diode (LED) lamps or LED light strips. The plurality of LED lamps or light strips are configured to generate UV-C light at a wavelength of approximately between 100 and 280 nanometers (nm). The sanitizing component further comprises a rechargeable battery.

The mask component is air permeable and comprises an inside layer, an outside layer, and a pocket disposed between the inside and outside layers. The pocket is configured to encapsulate the sanitizing component. The pocket may comprise a pocket liner and a closable opening. The pocket liner, the inside layer, the outside layer, or any combination thereof are configured to block UV light generated by the UV generating component.

The sanitizing face mask may further comprise a sanitizing component protective component. The sanitizing component protective component comprises a pair of outside layers and a pocket disposed between the pair of outside layers. The pocket may comprise a closable opening. The pocket is configured to accept and encapsulate the sanitizing component. The sanitizing component protective component is air permeable and is configured to block UV light. The pocket of the mask component is sized to accept and encapsulate the sanitizing component encapsulated within the sanitizing component protective component.

In an additional embodiment, the subject matter disclosed and claimed herein, comprises a sanitizing device for use with a face mask. The sanitizing device comprises sanitizing component. The sanitizing component comprises a base and an ultraviolet (UV) generating component incorporated into the base. The UV generating component comprises a plurality of light emitting diode (LED) lamps or LED light strips. The plurality of LED lamps or light strips are configured to generate UV-C light at a wavelength of approximately between 100 and 280 nanometers (nm). The sanitizing component further comprises a rechargeable battery.

The sanitizing device further comprises a sanitizing component protective component. The sanitizing component protective component comprises a pair of outside layers and a pocket disposed between the pair of outside layers. The pocket comprises a closable opening. The pocket is configured to accept and encapsulate the sanitizing component. The sanitizing component protective component is air permeable and is configured to block UV light. The sanitizing component protective component further comprises a mask attachment element for attaching the sanitizing component protective component to an outside layer of the face mask.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They do not intend as an exhaustive description of the invention or do not limit the scope of the invention. Additionally, an illustrated embodiment need not have all the aspects or advantages shown. Thus, in other embodiments, any of the features described herein from different embodiments may be combined.

The present invention, in one exemplary embodiment provides users with a modified protective face mask featuring an ultraviolet (UV) light filter capable of sanitizing inhaled and exhaled air. The face mask is configured to accept a UV light source within a built-in pocket in the face mask. As such, a user can remove the UV light source and recharge it as needed. The sanitizing face mask ensures that all inhaled and exhaled air is fully cleaned and sanitized by the UV light filter as a user breathes. The sanitizing face mask maximizes protection for the user and others against germs, bacteria, viruses, and other harmful pathogens improving the overall safety of public areas.

The sanitizing face mask comprises a personal protective face mask equipped with a filter pocket configured to receive and retain a UV light filter. The UV light filter may comprise a set of UV lights capable of being recharged for continuous use. Users may insert the UV light filter into the filter pocket for increased protection against harmful airborne pathogens. The outer or inner layers of the filter pocket may be constructed from a UV resistant or UV shielding material to protect users from constant exposure to the UV light filter insert. Traditional face masks may be modified to use the UV light filter.

When the UV filter is active within the face mask, the user may inhale and exhale air that is sanitized by the UV filter. Any air that passes through the UV filter is sanitized and cleaned of harmful microbes. The UV filter improves the safety of the user and anyone in close proximity to the wearer in public areas and medical treatment areas. The sanitizing face mask may be available in various colors, sizes, styles, and designs. The exact size, measurement, construction, and design specifications may vary upon further development and manufacturing.

Figure 1:
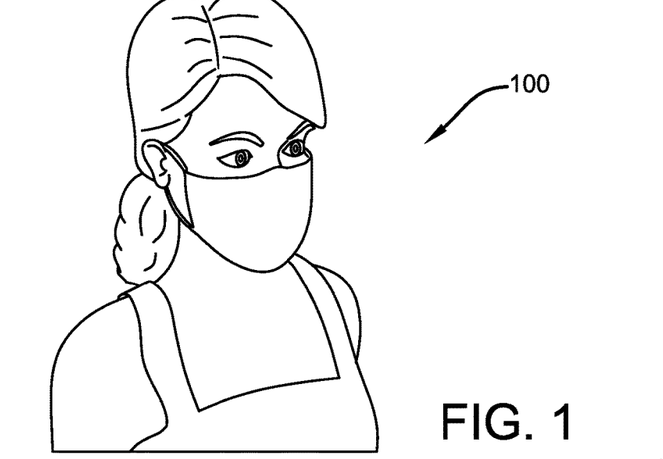
FIG. 1 illustrates a perspective view of one embodiment of a sanitizing face mask of the present invention in accordance with the disclosed architecture.
Figure 2:
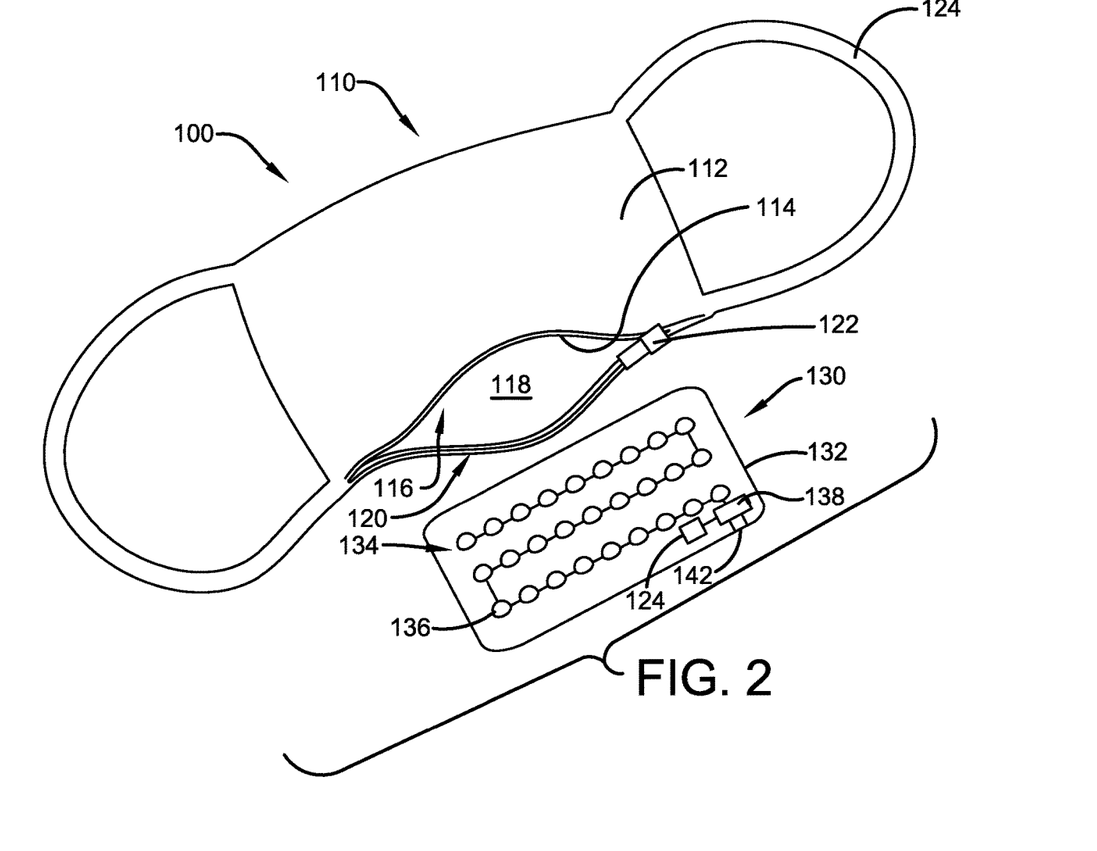
FIG. 2 illustrates an exploded view of a mask component and a sanitizing component of the sanitizing face mask of the present invention in accordance with the disclosed architecture.
Figure 3:
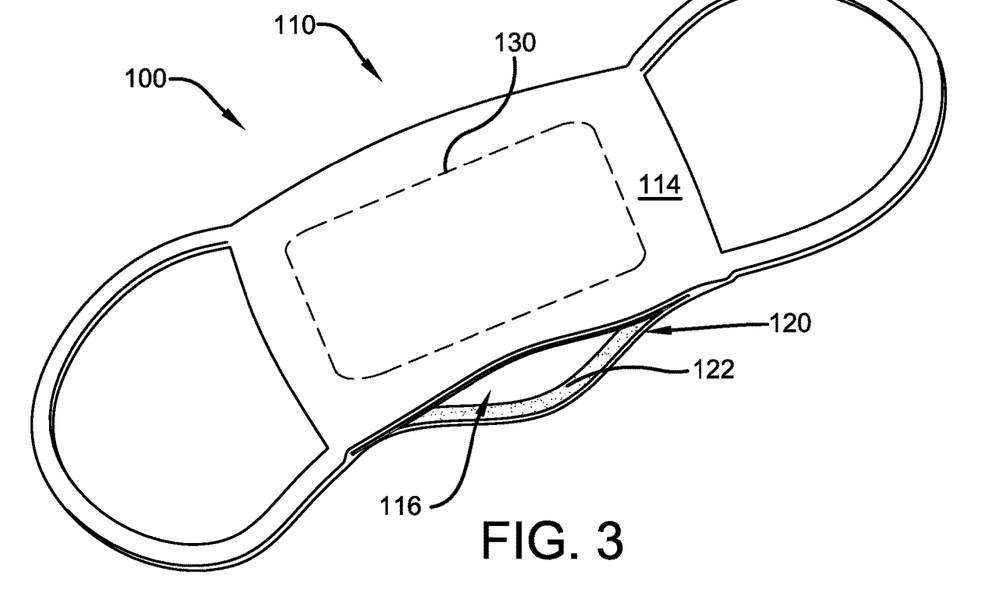
FIG. 3 illustrates a perspective view of the sanitizing component positioned within a packet of the mask component of the sanitizing face mask of the present invention in accordance with the disclosed architecture.
Figure 4:
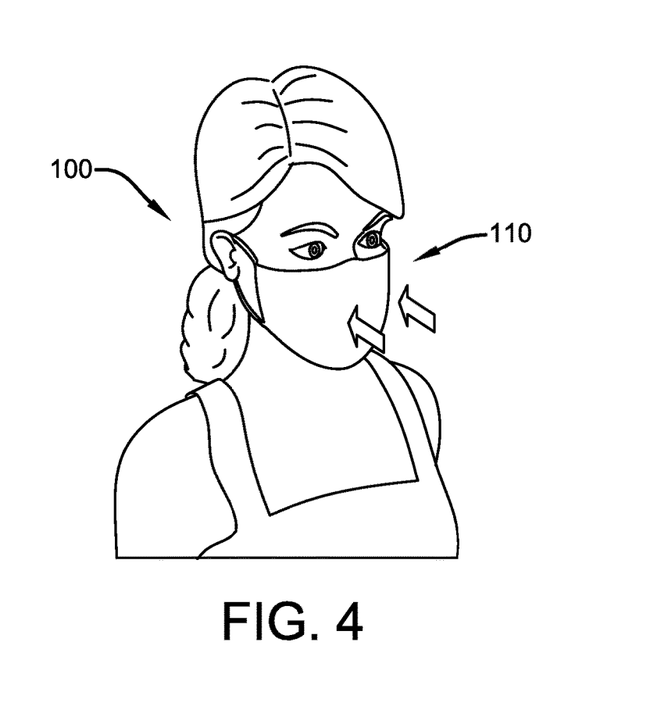
FIG. 4 illustrates a perspective view of non-sanitized air being inhaled through the sanitizing facemask of the present invention in accordance with the disclosed architecture.
Figure 5:
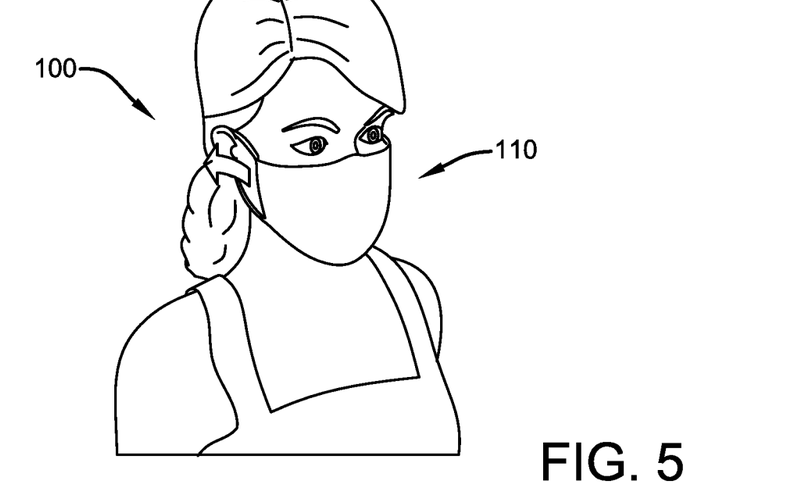
FIG. 5 illustrates a perspective view of sanitized air that has passed through the sanitizing face mask of the present invention exiting the sanitizing face mask in accordance with the disclosed architecture.
Figure 6:
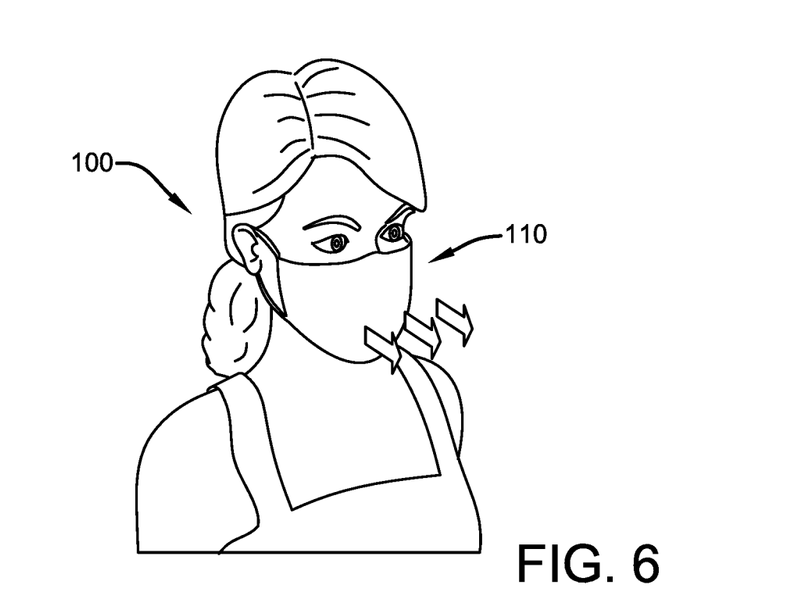
FIG. 6 illustrates a perspective view of sanitized air being exhaled through the sanitizing face mask of the present invention in accordance with the disclosed architecture.

Referring initially to the drawings, FIGS. 1-8 illustrate a sanitizing face mask 100. As a user inhales potentially contaminated air through the sanitizing face mask 100 as illustrated in FIG. 4, the sanitizing face mask 100 sanitizes the air before reaching the user and any un-inhaled sanitized air may exit the sanitizing face mask 100 as illustrated in FIG. 5. Similarly, potentially contaminated exhaled air from the user is sanitized as it passes through the sanitizing face mask 100 as illustrated in FIG. 6.

As illustrated in FIG. 2, the sanitizing face mask 100 comprises a mask component 110 and a sanitizing component 130. The sanitizing component 130 comprises a base 132 and an ultraviolet (UV) generating component 134 incorporated into the base 132. The base 132 may be manufactured from plastic, card stock, ribbon, film, or any other material suitable for this purpose as is known in the art.. The UV generating component 134 comprises a plurality of light emitting diode (LED) lights 136 configured as LED lamps or LED strips. The plurality of LED lights 136 are configured to generate UV-C light at a wavelength of approximately between 100 and 280 nanometers (nm). The sanitizing component 130 further comprises a rechargeable battery 138 and a recharging port 142 incorporated into the base in electrical communication with the UV generating component 134. The sanitizing component 130 further comprises an on/off switch 140 for activating and deactivating the UV generating component 134.

The mask component 110 is air permeable and typically constructed from a cloth or fabric material. The mask component 110 comprises an inside layer 114, an outside layer 112, and a pocket 116 disposed between the inside and outside layers 114 and 112. The pocket 116 is configured to encapsulate the sanitizing component 130 as illustrated in FIG. 3. The pocket 116 may comprise a pocket liner 118 and a closable opening 120. The closable opening 120 may comprise a fastener 122, such as a zipper, buttons, snaps, Velcro, or other similar mechanical fastening device.

The pocket liner 118 is typically constructed from an air permeable fabric material that is dyed, tightly woven, or luminous to prevent transmission of the UV light outside of the sanitizing face mask. Similarly, the inside layer 114, the outside layer 112, or any combination thereof may also be configured to block UV light generated by the UV generating component 134. The pocket liner 118, the outside layer 112, the inside layer 114, or any combination thereof are manufactured to have a UV protection factor of at least approximately 50 allowing no more than 2% of UV rays to penetrate the material. The mask component 110 further comprises a pair of ear loops 124 or head straps (not shown) for keeping the mask component 110 when donned by the user.

Figure 7:
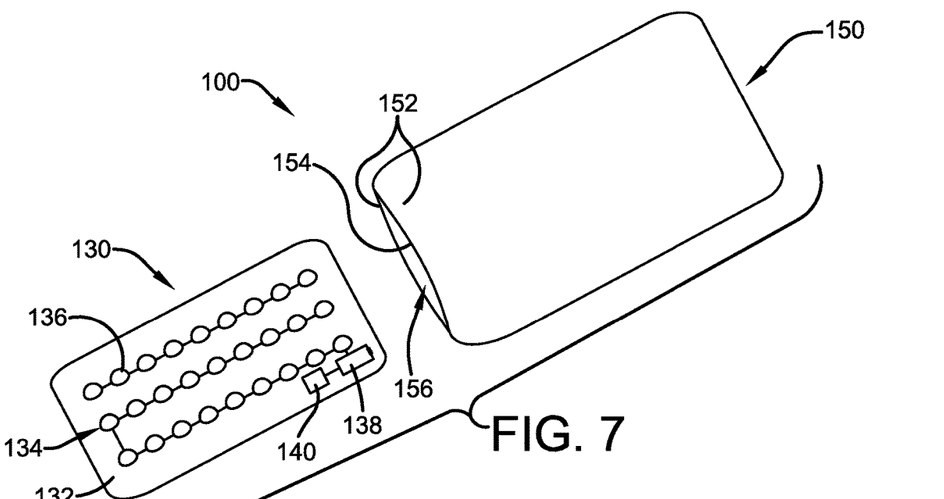
FIG. 7 illustrates an exploded view of the sanitizing component and a sanitizing component protective component of the sanitizing face mask of the present invention in accordance with the disclosed architecture.
Figure 8:
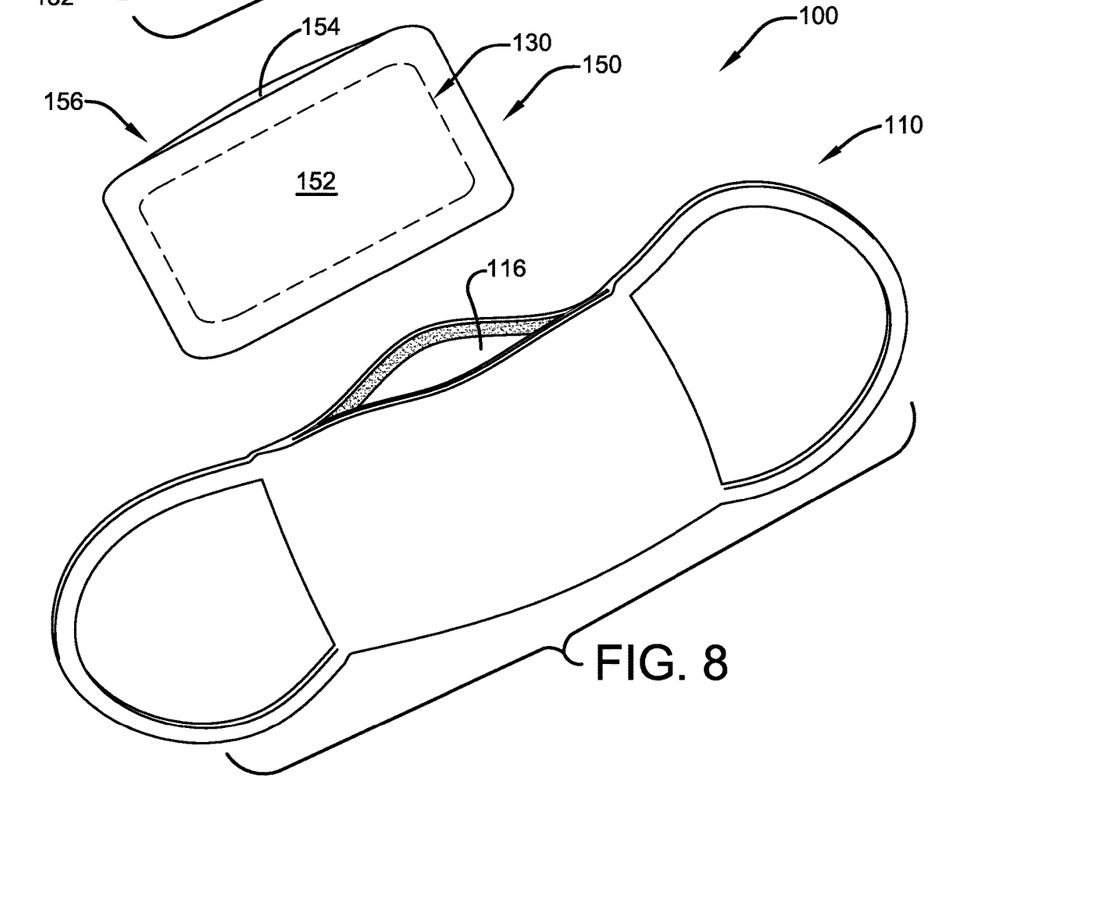
FIG. 8 illustrates an exploded view of the sanitizing component protective component and the mask component of the sanitizing face mask of the present invention in accordance with the disclosed architecture.

As illustrated in FIGS. 7 and 8, the sanitizing face mask 100 may further comprise a sanitizing component protective component 150. The sanitizing component protective component 150 comprises a pair of outside layers 152 and a pocket 154 disposed between the pair of outside layers 152. The pocket 154 may comprise a closable opening 156 similar to the closable opening 120 of the pocket 116 of the mask component 110. The pocket 154 is configured to accept and encapsulate the sanitizing component 130. The sanitizing component protective component 150 is manufactured from a similar material as the mask component 110 and is air permeable and configured to block UV light. The pocket 116 of the mask component 110 is sized to accept and encapsulate the sanitizing component 130 encapsulated within the sanitizing component protective component 150.

Figure 9:
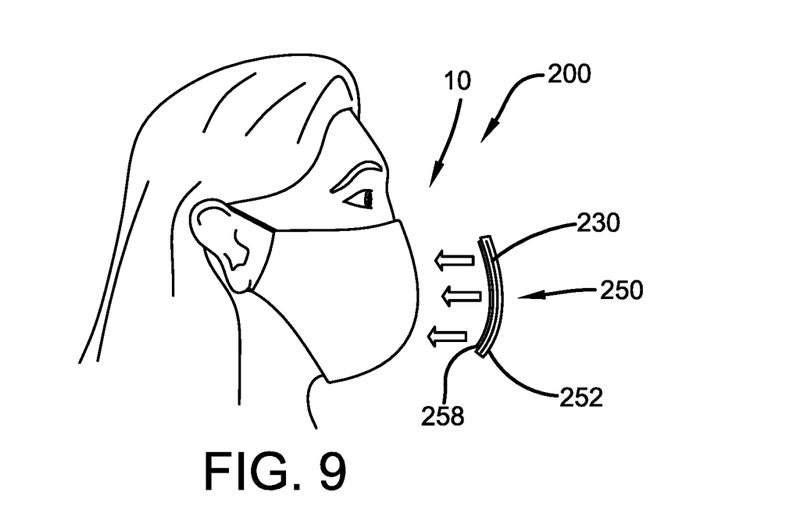
FIG. 9 illustrates an exploded view of a sanitizing device of the present invention for use with a face mask in accordance with the disclosed architecture.
Figure 10:
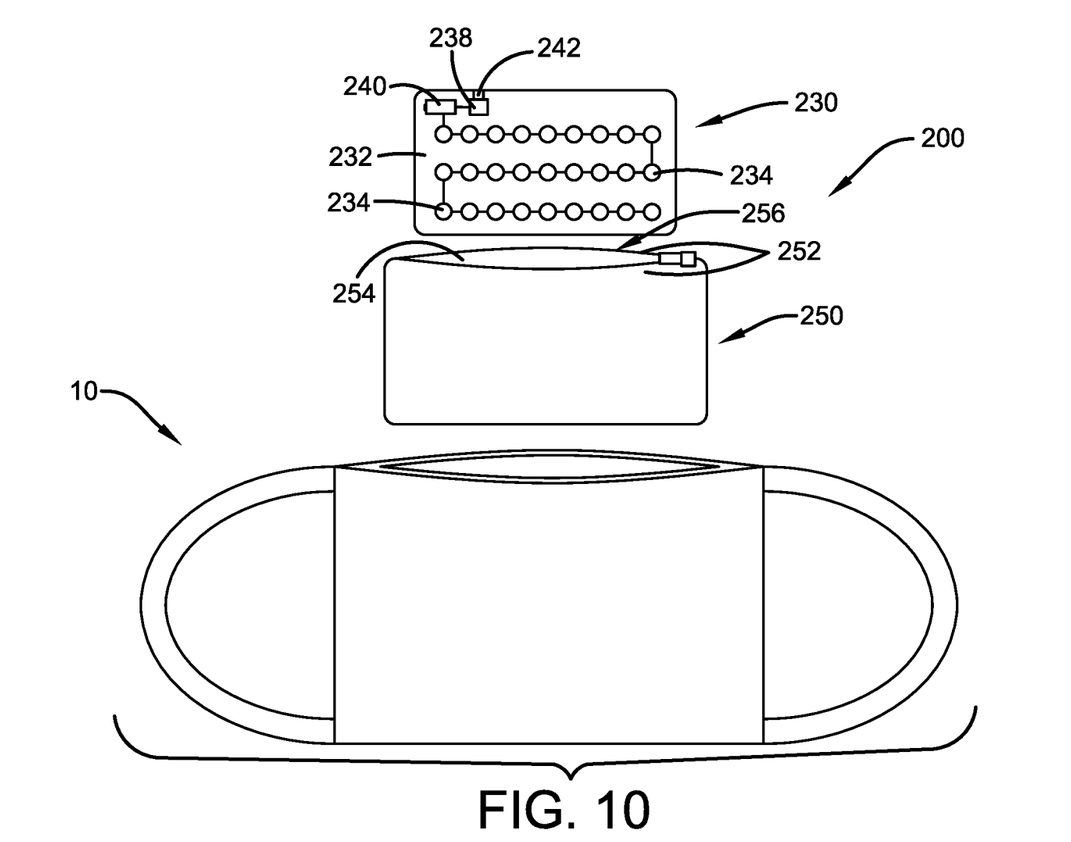
FIG. 10 illustrates a side view of the sanitizing device of the present invention attaching to the face mask in accordance with the disclosed architecture.

In an additional embodiment as illustrated in FIGS. 9 and 10, a sanitizing device 200 for use with a face mask 10 is disclosed. The sanitizing device 200 comprises sanitizing component 230. The sanitizing component 230 comprises a base 232 and an ultraviolet (UV) generating component 234 incorporated into the base 232. The base 232 may be manufactured from plastic, card stock, ribbon, film, or the like. The UV generating component 234 comprises a plurality of light emitting diode (LED) lights (similar to 136) configured as LED lamps or LED strips. The plurality of LED lights are configured to generate UV-C light at a wavelength of approximately between 100 and 280 nanometers (nm). The sanitizing component 230 further comprises a rechargeable battery 238 and a recharging port 242 incorporated into the base in electrical communication with the UV generating component 234. The sanitizing component 230 further comprises an on/off switch 240 for activating and deactivating the UV generating component 234.

The sanitizing device 200 further comprises a sanitizing component protective component 250. The sanitizing component protective component 250 comprises a pair of outside layers 252 and a pocket 254 disposed between the pair of outside layers 252. The pocket 254 may comprise a closable opening 256. The closable opening 256 may comprise a fastener (similar to 122), such as a zipper, buttons, snaps, Velcro, or other similar mechanical fastening device. The pocket 254 is configured to accept and encapsulate the sanitizing component 230. The sanitizing component protective component 250 is manufactured from an air permeable fabric material that is dyed, tightly woven, or luminous to prevent transmission of the UV light outside of the sanitizing component protective component 250.

As illustrated in FIG. 9, the sanitizing component protective component 250 may further comprise a mask attachment element 258. The mask attachment element 258 may be incorporated or attached to one of the outside layers 252. The mask attachment element 250 is used to attach the sanitizing component protective component 258 to the face mask 10. The mask attachment element 258 may be manufactured from Velcro or an adhesive that will engage on outer surface of the face mask 10.

It is contemplated that the sanitizing face mask 100 and the sanitizing device 200 for use with the face mask 10 constructed in accordance with the present invention will be tailored and adjusted by those of ordinary skill in the art to accommodate various levels of performance demand imparted during actual use. Accordingly, while this invention has been described by reference to certain specific embodiments and examples, it will be understood that this invention is capable of further modifications. This application is, therefore, intended to cover any variations, uses or adaptations of the invention following the general principles thereof, and including such departures from the present disclosure as come within known or customary practice in the art to which this invention pertains and fall within the limits of the appended claims.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A sanitizing device comprising:
   a sanitizing component comprising a base and an ultraviolet (UV) light generating component incorporated into the base; and
   a sanitizing component protective component for encapsulating the sanitizing component; and
   a face mask comprising a pocket; and
   wherein the sanitizing component protective component is positional within the pocket of the face mask.

2. The sanitizing device of claim 1, wherein the sanitizing component protective component is configured to block UV light.

3. The sanitizing device of claim 1, wherein the sanitizing component protective component is air permeable.

4. The sanitizing device of claim 1, wherein the sanitizing component generates UV light in a wavelength of between 100 and 280 nanometers.

5. The sanitizing device of claim 1, wherein the sanitizing component is rechargeable.

6. A sanitizing face mask comprising:
   a sanitizing component comprising a base and an ultraviolet (UV) light generating component incorporated into the base; and
   a sanitizing component protective component for encapsulating the sanitizing component; and
   a mask component comprising a pocket for encapsulating the sanitizing component within the sanitizing component protective component.

7. The sanitizing face mask of claim 6, wherein the pocket is configured to block UV light.

8. The sanitizing face mask of claim 6, wherein the mask component comprises an inside layer configured to block UV light.

9. The sanitizing face mask of claim 6, wherein the mask component is air permeable.

10. The sanitizing face mask of claim 6, wherein the ultraviolet (UV) light generating component comprises a plurality of UV lights.

11. The sanitizing face mask of claim 10, wherein the plurality of UV lights generate UV light in a wavelength of between 100 and 280 nanometers.

12. The sanitizing face mask of claim 6, wherein the pocket comprises a closable opening.

13. The sanitizing face mask of claim 6, wherein the pocket has an UV protection factor of at least 50.

14. The sanitizing face mask of claim 6, wherein the sanitizing component is rechargeable.

15. A sanitizing face mask comprising:
    a sanitizing component comprising a base and an ultraviolet (UV) light generating component incorporated into the base;
    a sanitizing component protective component for encapsulating the sanitizing component; and
    a mask component comprising a pocket.

16. The sanitizing face mask of claim 15, wherein the sanitizing component protective component is air permeable.

17. The sanitizing face mask of claim 15, wherein the pocket or the sanitizing component protective component is configured to block UV light.

18. The sanitizing face mask of claim 15, wherein the pocket is configured to retain the sanitizing component encapsulated within the sanitizing component protective component.

19. The sanitizing face mask of claim 15, wherein the pocket comprises a closable opening.

20. The sanitizing face mask of claim 15, wherein the ultraviolet (UV) light generating component comprises a plurality of UV lights that generate UV light in a wavelength of between 100 and 280 nanometers.

* * * * *